(12) United States Patent
Chang et al.

(10) Patent No.: US 10,288,583 B2
(45) Date of Patent: May 14, 2019

(54) DEFECT DISCRIMINATION APPARATUS, METHODS, AND SYSTEMS

(71) Applicant: Halliburton Energy Services, Inc., Houston, TX (US)

(72) Inventors: Paul Chinling Chang, Houston, TX (US); Luis Emilio San Martin, Houston, TX (US); Reza Khalaj Amineh, Houston, TX (US); Aixa Maria Rivera-Rios, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/125,000

(22) PCT Filed: Nov. 10, 2015

(86) PCT No.: PCT/US2015/059931
§ 371 (c)(1),
(2) Date: Sep. 9, 2016

(87) PCT Pub. No.: WO2017/082874
PCT Pub. Date: May 18, 2017

(65) Prior Publication Data
US 2017/0261469 A1   Sep. 14, 2017

(51) Int. Cl.
*G01N 27/90* (2006.01)
*E21B 47/00* (2012.01)
*G01V 3/28* (2006.01)
*G01N 17/04* (2006.01)

(52) U.S. Cl.
CPC ............ *G01N 27/90* (2013.01); *E21B 47/00* (2013.01); *G01V 3/28* (2013.01); *G01N 17/04* (2013.01)

(58) Field of Classification Search
CPC .............................. G01N 27/90; G01N 17/04
See application file for complete search history.

(56) References Cited

U.S. PATENT DOCUMENTS

| 4,475,038 A | * | 10/1984 | Lochmann | G01V 5/101 250/269.6 |
| 4,780,266 A | * | 10/1988 | Jordan | E21B 47/1015 166/250.17 |
| 6,100,696 A | * | 8/2000 | Sinclair | G01V 3/28 324/338 |

(Continued)

FOREIGN PATENT DOCUMENTS

| EP | 2908124 A1 | 8/2015 | |
| WO | WO 2014035285 A1 * | 3/2014 | ............ E21B 47/00 |

(Continued)

OTHER PUBLICATIONS

"International Application Serial No. PCT/US2015/059931, International Search Report dated Aug. 9, 2016", 3 pgs.

(Continued)

*Primary Examiner* — Walter L Lindsay, Jr.
*Assistant Examiner* — Milton Gonzalez
(74) *Attorney, Agent, or Firm* — Gilliam IP PLLC

(57) ABSTRACT

An apparatus and a system, as well as methods, operable to include acquiring eddy current data from at least two concentric pipes, determining spatial frequency content of the eddy current data, and determining locations of defects in each of the pipes based on the spatial frequency content.

20 Claims, 12 Drawing Sheets

(56) References Cited

U.S. PATENT DOCUMENTS

| | | | |
|---|---|---|---|
| 6,628,118 B1 * | 9/2003 | Amini | G01V 3/28 324/239 |
| 6,630,831 B2 * | 10/2003 | Amini | G01V 3/28 324/339 |
| 7,764,572 B2 * | 7/2010 | Wu | G01V 1/44 181/102 |
| 2006/0202685 A1 | 9/2006 | Barolak et al. | |
| 2013/0193953 A1 | 8/2013 | Yarbro et al. | |
| 2016/0290966 A1 * | 10/2016 | Koenig | G01N 27/9053 |

FOREIGN PATENT DOCUMENTS

| WO | WO-2014189497 A1 | 11/2014 |
|---|---|---|
| WO | WO-2015050836 A1 | 4/2015 |

OTHER PUBLICATIONS

"International Application Serial No. PCT/US2015/059931, Written Opinion dated Aug. 9, 2016", 8 pgs.

\* cited by examiner

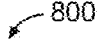

| | |
|---|---|
| Outer diameter (inches) | 2+7/8 (pipe 1), 4+1/2 (pipe 2), 9+5/8 (pipe 3), (OD)1<br>4+1/2 (pipe 1), 9+5/8 (pipe 2), 13+3/8 (pipe 3), (OD2) |
| Pipe thicknesses (inches) | 0.45 (pipe 1), 0.6 (pipe 2), 0.6 (pipe 3) |
| Pipe permeability (H/m) | 50, 100, 150 |
| Pipe conductivity (H/m) | 1 x 106 |
| Current (Amp) | 1 |
| Transmitter length (inches) | 8 |
| Number of coils (transmitter) | 1000 |
| Transmitter core permeability (H/m) | 200 |
| Receiver length (inches) | 4 |
| Number of coil turns (receiver) | 1600 |
| Receiver core permeability | 1 (air core) |
| Transmitter/Receiver core diameter (inches) | 1.2 |
| Defect thickness (inches) | 0.1, 0.2, 0.3 |
| Defect length (inches) | 5, 10 |
| Transmitter-Receiver spacing (inches) | 10, 20, 30 |
| Frequencies (Hz) | 2, 10 |
| Signal-to-noise ratio (dB) | 40 (1%) |
| Data acquisition rate (Hz) | 0.5 |
| Logging Speed (inches/second) | 1 |

Fig. 8

DEFECT DISCRIMINATION APPARATUS, METHODS, AND SYSTEMS

RELATED APPLICATIONS

This application is a U.S. National Stage Filing under 37 U.S.C. 371 of international Patent Application Serial No. PCT/US2015/059931, filed 10 Nov. 2015, the benefit of priority of which is claimed hereby and which is incorporated by reference herein in its entirety.

BACKGROUND

Hydrocarbon production may use metal pipes, disposed in a geological formation, to bring hydrocarbons to the surface. Since hydrocarbon production may occur over years or even decades, it is useful to monitor the condition of the pipes to determine whether corrosion has degraded the ability to isolate production zones.

Existing corrosion inspection tools can be used to provide estimates of total casing thickness. However, these tools, and the data processing techniques used in conjunction with them, do not enable evaluating the condition of individual, concentric pipes.

BRIEF DESCRIPTION OF THE DRAWINGS

FIG. 8 is a table of sensor configurations and pipe parameters for the downhole corrosion simulations of FIGS. 1-7.

DETAILED DESCRIPTION

Figure 1:
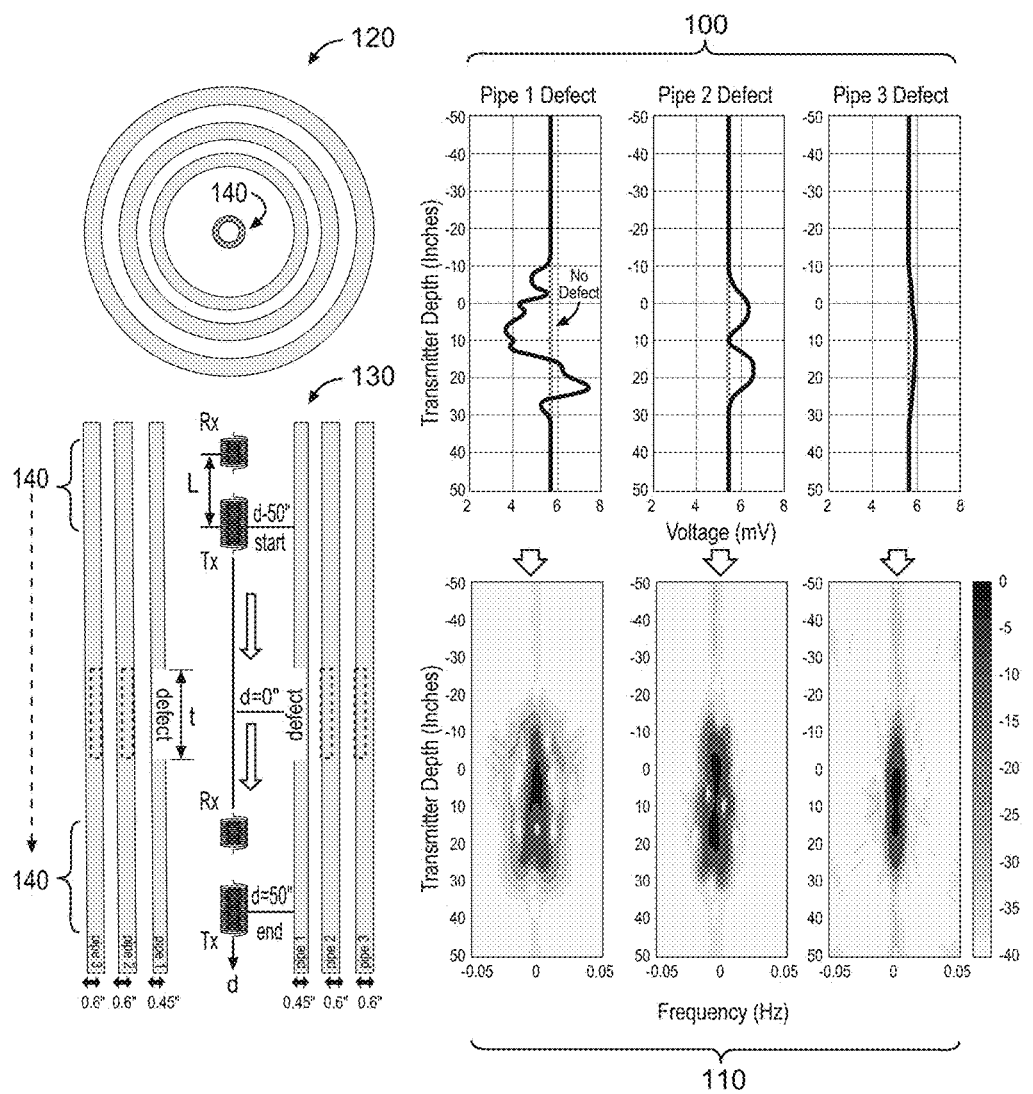
FIG. 1 illustrates received voltages and corresponding time-frequency spectrograms for downhole pipe corrosion simulations, according to various embodiments.

Existing corrosion inspection tools provide overall casing thickness estimates, operating to analyze the time-domain decay response to characterize the condition of tubing and casing together. The associated inversion processes are based on a comparison of the measured response with simulated responses contained in a library of pre-existing casing parameters. These existing combinations fail to provide a fast and reliable mechanism for characterizing individual defects that are present in concentric arrangements of pipe, due to corrosion and other degrading influences.

To address some of these challenges, as well as others, various embodiments have been developed to employ a time-frequency spectrogram to process frequency domain eddy current measurements for inspecting and monitoring tubing, casing, and other pipeline systems. Novel capabilities include the determination as to whether defects originate with inner or outer pipes in a concentric arrangement; providing an estimate of radial distance from the defects to the sensors; estimating the length of defects; using a range of frequencies to inspect over longer distances; and real-time processing for continuous operation and visualization while logging. Various aspects of some example embodiments will now be set forth in more detail.

Some embodiments provide methods of processing and interpreting electromagnetic (EM)-based data to inspect and monitor pipe corrosion. During the life of a well, the downhole environment may accelerate metal pipe corrosion, which can lead to well operation inefficiency, oil production cross-flows, leaks, and environmental damage. Thus, it is useful to monitor the condition of the pipes disposed in a geological formation.

In some embodiments, inspecting and monitoring the integrity of pipes can be done using a number of methods and tools. These tools include wireline-deployed tools, such as those that provide magnetic flux leakage (MFC) and eddy current (EC) measurements. These tools can also be used in slickline operations, where logging data is stored, and retrieved once the tool returns to the surface.

When making eddy current measurements, corrosion evaluation tools can be categorized into two groups: (1) time domain tools (pulsed eddy current) or (2) frequency domain tools (commonly known as the eddy current or remote field eddy current). In operating time domain tools, a transmitting coil sends pulsed signals generating electromagnetic fields that induce eddy currents in surrounding pipes. Once the transmitter is turned off, one or more receiving coils record the electromotive voltages produced by the eddy currents in the pipes.

Frequency domain tools, on the other hand, transmit continuous sinusoidal waves and record induced voltages at the receivers. While time domain tools provide information across a larger frequency bandwidth, frequency domain tools may be more useful in exploiting frequency-specific characteristics of the pipes, such as using lower frequencies for better penetration depth into a series of concentric pipes. Thus, some embodiments employ a frequency domain eddy current technique that is applied at a single frequency, instead of a broadband, time domain (e.g., pulsed) technique.

Some embodiments described herein also use a time-frequency spectrogram to process and interpret frequency domain EC measurements to provide information that can be used for pipe defect detection and assessment. Advantages that may accrue include:

the technique is applicable to single-frequency EC downhole measurements (e.g., relatively low frequencies that can penetrate multiple pipes);

local frequency content of the time-varying voltage output can be used for pipe defect discrimination;

the radial location of defects can be determined (e.g., whether a defect is in the inner tubing or outer pipes);

defect size and length can be characterized; and
real-time monitoring and visualization of pipe condition can be employed.

In the following discussion of FIGS. 1-7, numerical simulation results are presented to illustrate representative responses which may be obtained using various embodiments. In order to characterize the impact of a pipe defect on the voltage at the receiver Rx, frequency-domain electromagnetic simulations for realistic downhole measurements have been carried out in a borehole containing three pipes (pipe1, pipe2, pipe3). In each case, receiver Rx voltages were sampled at different depths as the transmitter-receiver pair (Tx, Rx) moved past one or more defects in the pipes, the defects being centered at d=0 inches.

The simulations generally include three concentric pipes as a non-limiting example; any number of pipes may be employed, with at least two in most embodiments. Differences in response from defects in the first and second pipes, and sometimes the third pipe, are generally shown. Sensitivity to variations in the size of defects (e.g., length and depth), pipe permeability, pipe outer diameter, inspection frequency, and the distance between the transmitter and receiver in the transmitter-receiver pair (Tx, Rx).

FIG. 1 illustrates received voltages 100 and corresponding time-frequency spectrograms 110 for downhole pipe corrosion simulations, according to various embodiments. Here the received voltages 100, and the corresponding time-frequency spectrograms 110 are shown. The shading legend to the right of the spectrograms 110 indicate a vertical scale of decibels (dB) down from a maximum response amplitude (at 0 dB) over the data acquisition cycle for each pipe, and each defect. The horizontal scale for each of the spectrograms is a magnified one, representing a range of plus/minus the sampling rate, divided by two.

Figure 5:
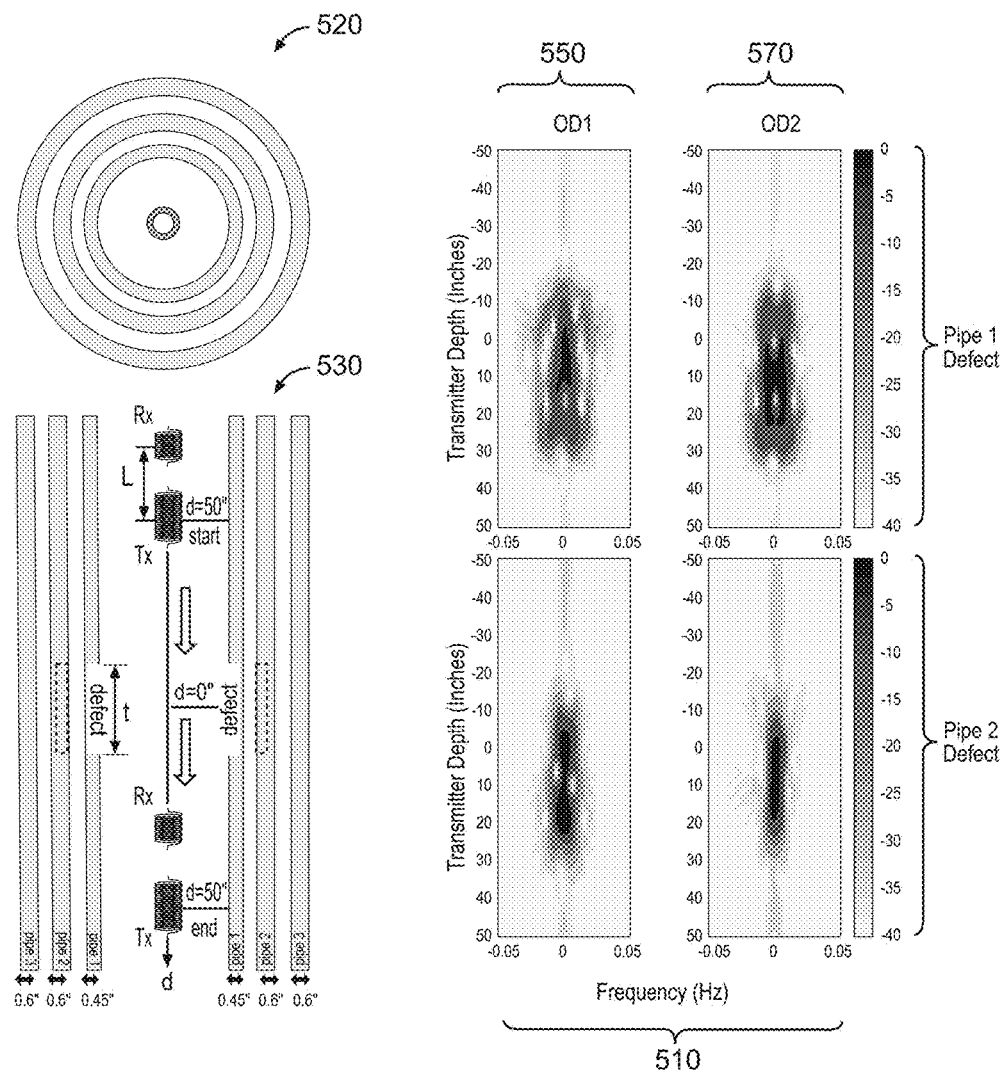
FIG. 5 illustrates time-frequency spectrograms for downhole corrosion simulations with varying pipe outer diameters, according to various embodiments.

The spectrograms 110 give a visual indication (and are useful for machine vision image processing) of known defects in three pipes (i.e., pipe1, pipe2, pipe3; shown in a top view 120, and side view 130) to simulate the effects of downhole corrosion. The pipes in this figure, and in all figures except FIG. 5, are disposed in a concentric arrangement with a series of outside diameters designated "OD1", wherein pipe1 has an outside diameter of 2⅞" (with a wall thickness of 0.45"), pipe2 has an outside diameter of 4½" (with a wall thickness of 0.6"), and pipe3 has an outside diameter of 9⅝" (with a wall thickness of 0.6").

To obtain the spectrograms 110, a data acquisition frequency of 0.5 Hz, an inspection frequency of 2 Hz, and a transmitter-receiver pair 140 (Tx, Rx) separation distance L=20 inches were used, in this figure, the defects in each pipe are the same size: defect length t=10 inches, and defect depth is 0.3 inch.

All pipes have a relative permeability of 50 in this figure. As is known to those of ordinary skill in the art, the relative permeability is the ratio between the permeability of a specific medium (e.g., one of the pipes) and free space permeability ($4\pi \times 10^7$ H/m)).

The side view 130 of the pipes shows an explicit defect around the inner perimeter of pipe1, with identical defects in dashed-line form for pipe2 and pipe3. These three defects are used to derive the receiver responses, in the form of voltages 100, to produce the corresponding spectrograms 110 for each of the pipes pipe1, pipe2, pipe3 as the transmitter-receiver pair 140 moves over a distance d=−50" to d=+50".

Figure 2:
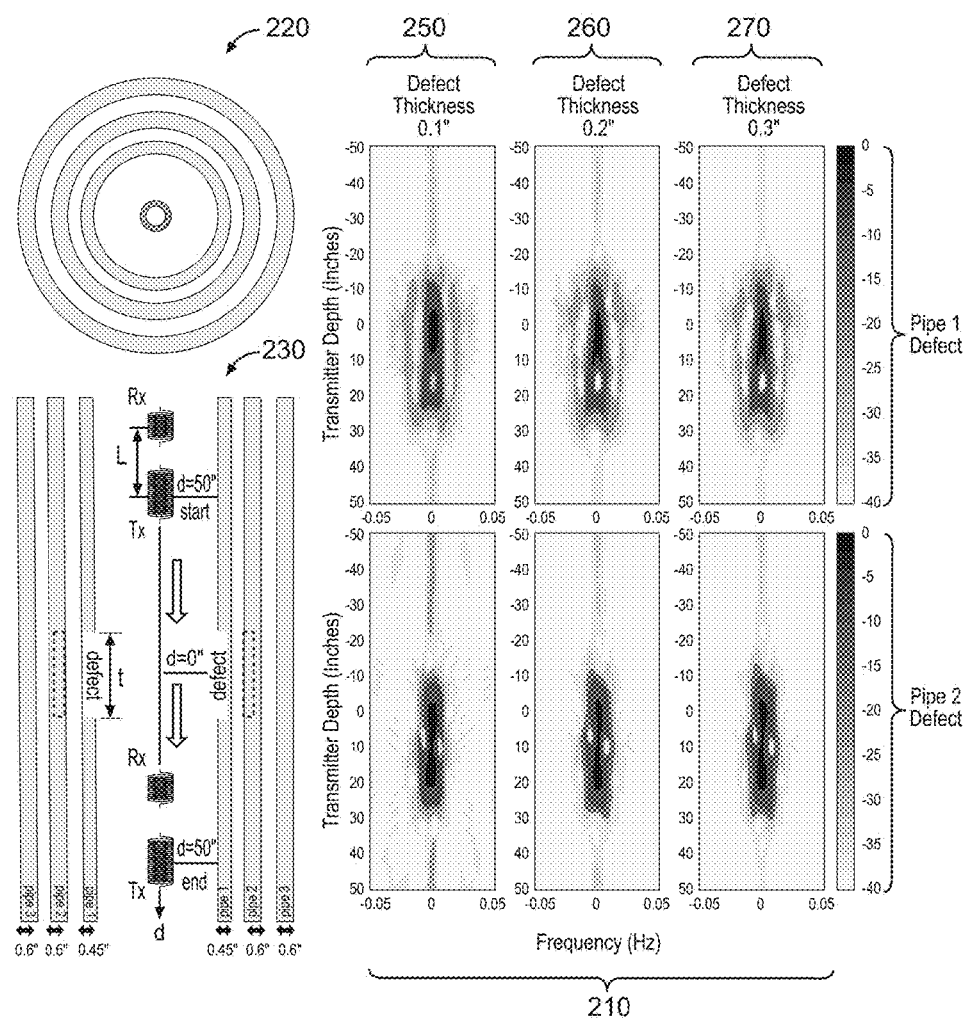
FIG. 2 illustrates time-frequency spectrograms for downhole corrosion simulations with varying pipe defect thicknesses, according to various embodiments.

FIG. 2 illustrates time-frequency spectrograms 210 for downhole corrosion simulations with varying pipe defect thicknesses, according to various embodiments. Again, the shading legend to the right of the spectrograms 210 indicate a vertical scale of decibels (dB) down from a maximum response amplitude (at 0 dB) over the data acquisition cycle for each pipe, and each defect. The horizontal scale for each of the spectrograms is a magnified one, representing a range of plus/minus the sampling rate, divided by two.

The spectrograms 210 give a visual indication (and are useful for machine vision image processing) of known defects in two pipes (i.e., pipe1 and pipe2; shown in a top view 220, and side view 230) to simulate the effects of downhole corrosion. The pipes in this figure are disposed in a concentric arrangement with the series of outside diameters designated OD1.

To obtain the spectrograms 210, a data acquisition frequency of 0.5 Hz, an inspection frequency of 2 Hz, and a transmitter-receiver pair (Tx, Rx) separation distance L=20 inches were used. In this figure, the defects in each pipe are the same size, but change in depth as the spectrograms 210 are displayed from left to right: the defect length t=10 inches, but the defect depth varies from 0.1" in the left set 250 of spectrograms 210, to 0.2" in the center set 260 of spectrograms 210, to 0.3" in the right set 270 of spectrograms 210.

All pipes have a relative permeability of 50 in this figure. The side view 230 of the pipes shows an explicit defect around the inner perimeter of pipe1, with a defect in dashed-line form for pipe2. These two defects are used to derive the receiver responses, to produce the corresponding spectrograms 210 for each of the pipes pipe1, pipe2 as the transmitter-receiver pair (Tx, Rx) moves over a distance d=−50" to d=+50".

Figure 3:
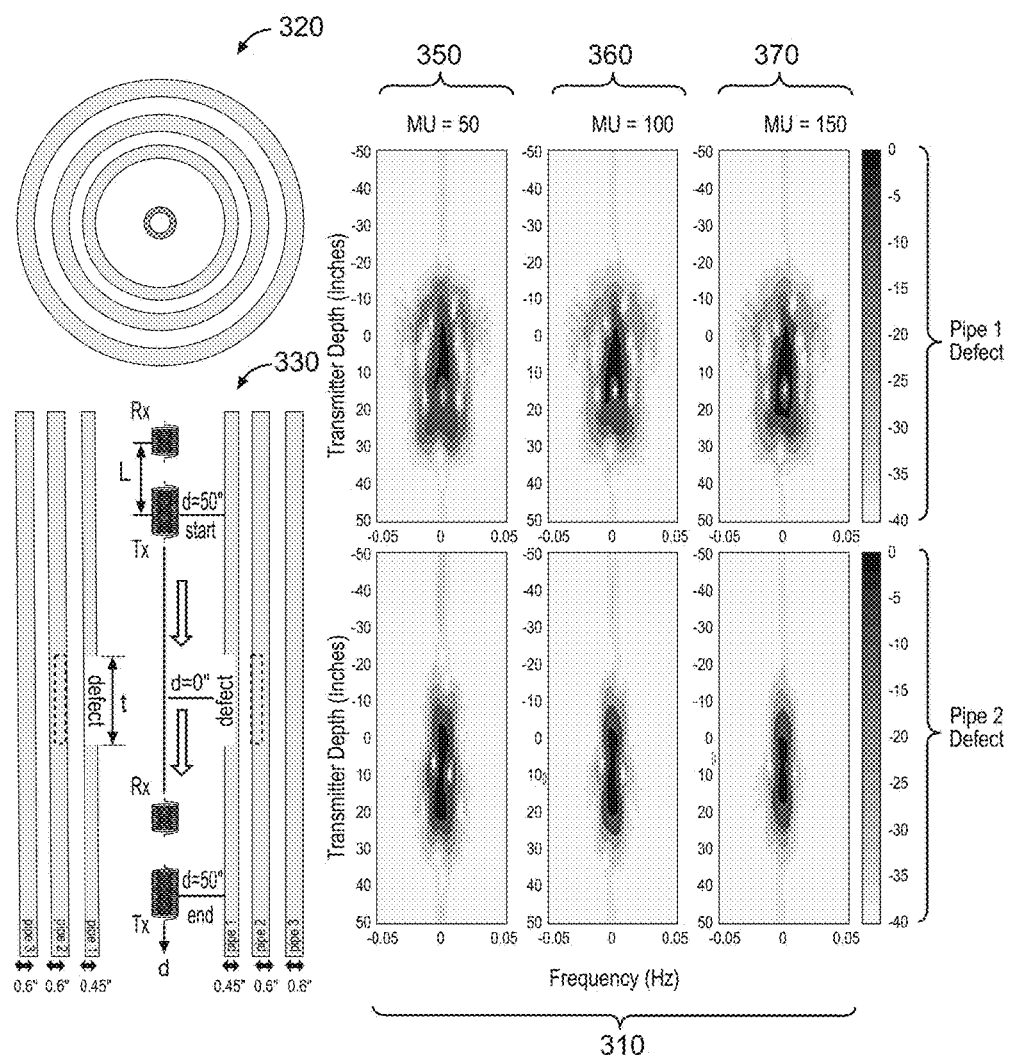
FIG. 3 illustrates time-frequency spectrograms for downhole corrosion simulations with varying pipe permeability, according to various embodiments.

FIG. 3 illustrates time-Frequency spectrograms 310 for downhole corrosion simulations with varying pipe permeability, according to various embodiments. Again, the shading legend to the right of the spectrograms 310 indicate a vertical scale of decibels (dB) down from a maximum response amplitude (at 0 dB) over the data acquisition cycle for each pipe, and each defect. The horizontal scale for each of the spectrograms is a magnified one, representing a range of plus/minus the sampling rate, divided by two.

The spectrograms 310 give a visual indication (and are useful for machine vision image processing) of known defects in two pipes (i.e., pipe1 and pipe2; shown in a top view 320, and side view 330) to simulate the effects of downhole corrosion. The pipes in this figure are disposed in a concentric arrangement with the series of outside diameters designated OD1.

To obtain the spectrograms 310, a data acquisition frequency of 0.5 Hz, an inspection frequency of 2 Hz, and a transmitter-receiver pair (Tx, Rx) separation distance L=20 inches were used, in this figure, the defects in each pipe are the same size: defect length t=10 inches, and defect depth is 0.3 inch.

In this figure, the permeability of the pipes changes as the spectrograms 310 are displayed from left to right: the relative permeability for pipe1, pipe2 varies from 50 in the left set 350 of spectrograms 310, to 100 in the center set 360 of spectrograms 310, to 150 in the right set 370 of spectrograms 310. The side view 330 of the pipes shows an explicit defect around the inner perimeter of pipe1, with a defect in dashed-line form for pipe2. These two defects are used to derive the receiver responses, to produce the corresponding spectrograms 310 for each of the pipes pipe1, pipe2 as the transmitter-receiver pair (Tx, Rx) moves over a distance d=−50" to d=+50".

Figure 4:
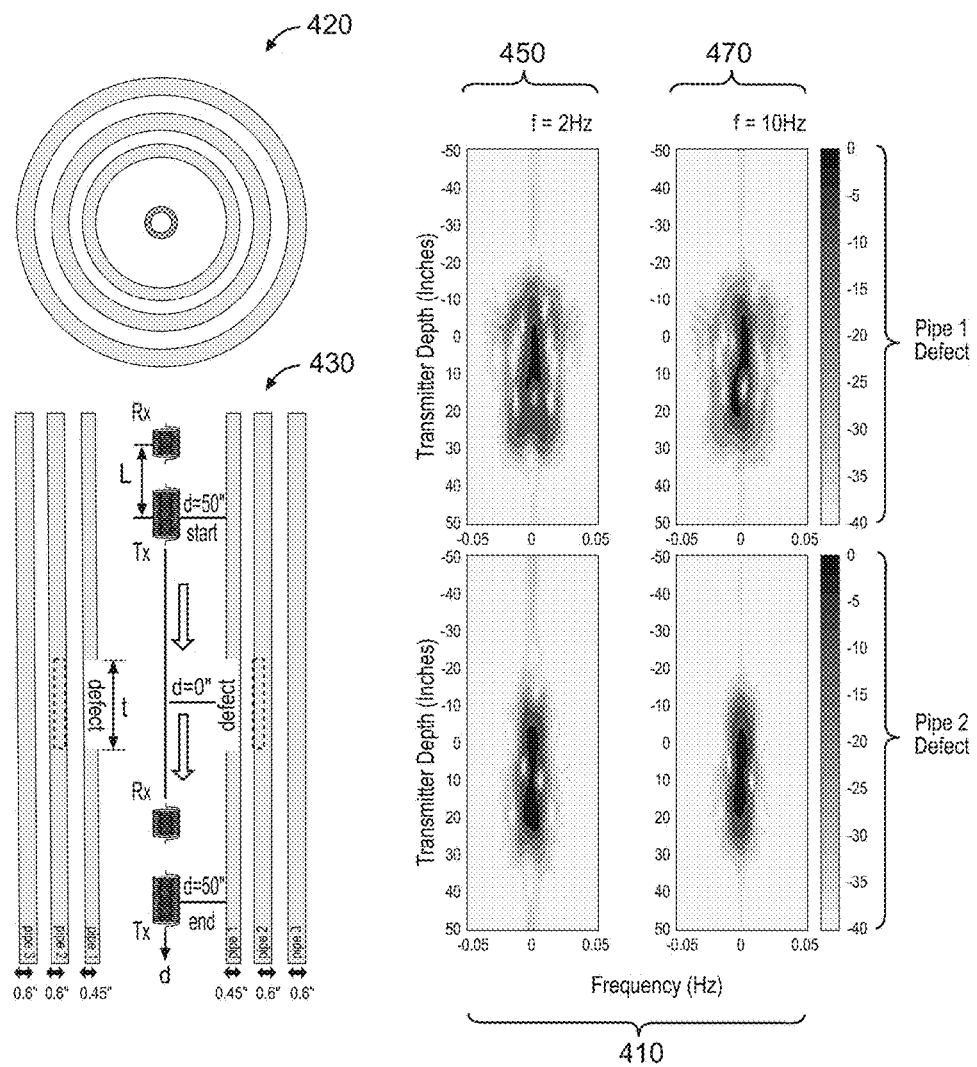
FIG. 4 time-frequency spectrograms for downhole corrosion simulations with varying inspection frequencies, according to various embodiments.

FIG. 4 time-frequency spectrograms 410 for downhole corrosion simulations with varying inspection frequencies, according to various embodiments. Again, the shading legend to the right of the spectrograms 410 indicate a vertical scale of decibels (dB) down from a maximum response amplitude (at 0 dB) over the data acquisition cycle for each pipe, and each defect. The horizontal scale for each of the spectrograms is a magnified one, representing a range of plus/minus the sampling rate, divided by two.

The spectrograms 410 give a visual indication (and are useful for machine vision image processing) of known defects in two pipes (i.e., pipe1 and pipe2; shown in a top view 420, and side view 430) to simulate the effects of downhole corrosion. The pipes in this figure are disposed in a concentric arrangement with the series of outside diameters designated OD1.

To obtain the spectrograms 410, a data acquisition frequency of 0.5 Hz was used, with a transmitter-receiver pair (Tx, Rx) separation distance L 20 inches were used. In this figure, the defects in each pipe are the same size: defect length t=10 inches, and defect depth is 0.3 inch. The relative permeability of the pipes is also the same value: 50.

In this figure, the inspection frequency of the pipes changes as the spectrograms 410 are displayed from left to right: the inspection frequency pipe1, pipe2 varies from 2 Hz in the left set 450 of spectrograms 410, to 10 Hz in the right set 470 of spectrograms 410. The side view 430 of the pipes shows an explicit defect around the inner perimeter of pipe1, with a defect in dashed-line form for pipe2. These two defects are used to derive the receiver responses, to produce the corresponding spectrograms 410 for each of the pipes pipe1, pipe2 as the transmitter-receiver pair (Tx, Rx) moves over a distance d=−50" to d=+50".

FIG. 5 illustrates time-frequency spectrograms 510 for downhole corrosion simulations with varying pipe outer diameters, according to various embodiments. Again, the shading legend to the right of the spectrograms 510 indicate a vertical scale of decibels (dB) down from a maximum response amplitude (at 0 dB) over the data acquisition cycle for each pipe, and each defect. The horizontal scale for each of the spectrograms is a magnified one, representing a range of plus/minus the sampling rate, divided by two.

The spectrograms 510 give a visual indication (and are useful for machine vision image processing) of known defects in two pipes (i.e., pipe1, pipe2; shown in a top view 520, and side view 530) to simulate the effects of downhole corrosion. The pipes in this figure, unlike those of the other figures, are disposed in a concentric arrangement with a series of outside diameters designated "OD1" in a first simulation, and "OD2" in a second simulation. For arrangement OD2, pipe1 has an outside diameter of 4½" (with a wall thickness of 0.45"), pipe2 has an outside diameter of 9⅝" (with a wall thickness of 0.6"), and pipe3 has an outside diameter of 13⅜" (with a wall thickness of 0.6"). Thus, in this figure, the outer diameter of the series of pipes changes as the spectrograms 510 are displayed from left to right: arrangement OD1 is used in the left set 550 of spectrograms 510, and arrangement OD2 is used in the right set 570 of spectrograms 510.

To obtain the spectrograms 510, a data acquisition frequency of 0.5 Hz, an inspection frequency of 2 Hz, and a transmitter-receiver pair (Tx, Rx) separation distance L=20 inches was used. In this figure, the defects in each pipe are the same size: defect length t=10 inches and defect depth is 0.3 inch.

All pipes have a relative permeability of 50 in this figure. The side view 530 of the pipes shows an explicit defect around the inner perimeter of pipe1, with a defect in dashed-line form for pipe2. These two defects are used to derive the receiver responses, to produce the corresponding spectrograms 510 for each of the pipes pipe1, pipe2 as the transmitter-receiver pair (Tx, Rx) moves over a distance d=−50" to d=+50".

Figure 6:
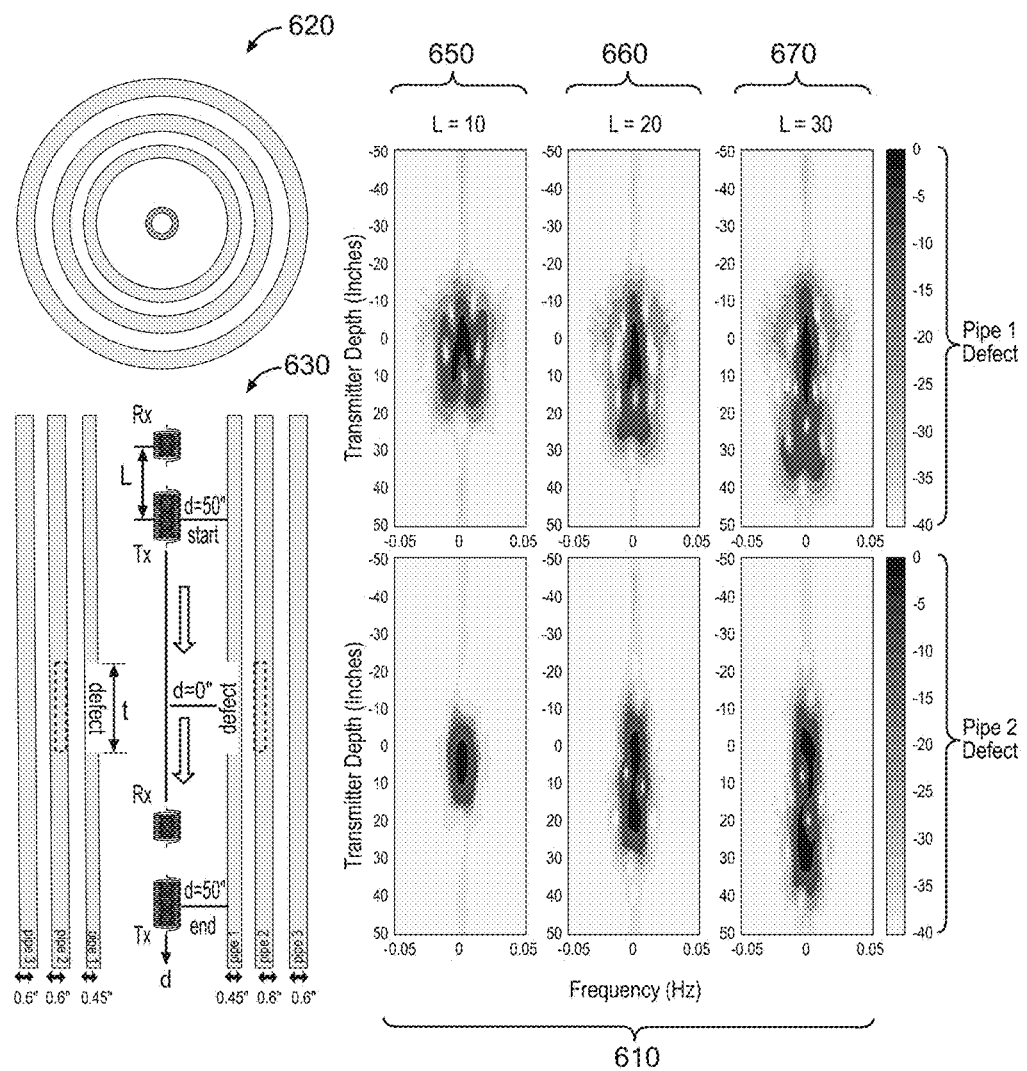
FIG. 6 illustrates time-frequency spectrograms for downhole corrosion simulations with varying transmitter-receiver spacing, according to various embodiments.

FIG. 6 illustrates time-frequency spectrograms 610 for downhole corrosion simulations with varying transmitter-receiver spacing, according to various embodiments. Again, the shading legend to the right of the spectrograms 610 indicate a vertical scale of decibels (dB) down from a maximum response amplitude (at 0 dB) over the data acquisition cycle for each pipe, and each defect. The horizontal scale for each of the spectrograms is a magnified one, representing a range of plus/minus the sampling rate, divided by two.

The spectrograms 610 give a visual indication (and are useful for machine vision image processing) of known defects in two pipes (i.e., pipe1 and pipe2; shown in a top view 620, and side view 630) to simulate the effects of downhole corrosion. The pipes in this figure are disposed in a concentric arrangement with the series of outside diameters designated OD1.

To obtain the spectrograms 610, a data acquisition frequency of 0.5 Hz, and an inspection frequency of 2 Hz were used. In this figure, the defects in each pipe are the same size: defect length t=10 inches, and defect depth is 0.3 inch.

In this figure, the transmitter-receiver pair (Tx, Rx) separation distance L changes as the spectrograms 610 are displayed from left to right: the separation distance L varies from L=10" in the left set 650 of spectrograms 610, to L=20" in the center set 660 of spectrograms 610, to L=30" in the right set 670 of spectrograms 610. The side view 630 of the pipes shows an explicit defect around the inner perimeter of pipe1, with a defect in dashed-line form for pipe2. These two defects are used to derive the receiver responses, to produce the corresponding spectrograms 610 for each of the pipes pipe1, pipe2 as the transmitter-receiver pair (Tx, Rx) moves over a distance d=−50" to d=+50".

Figure 7:
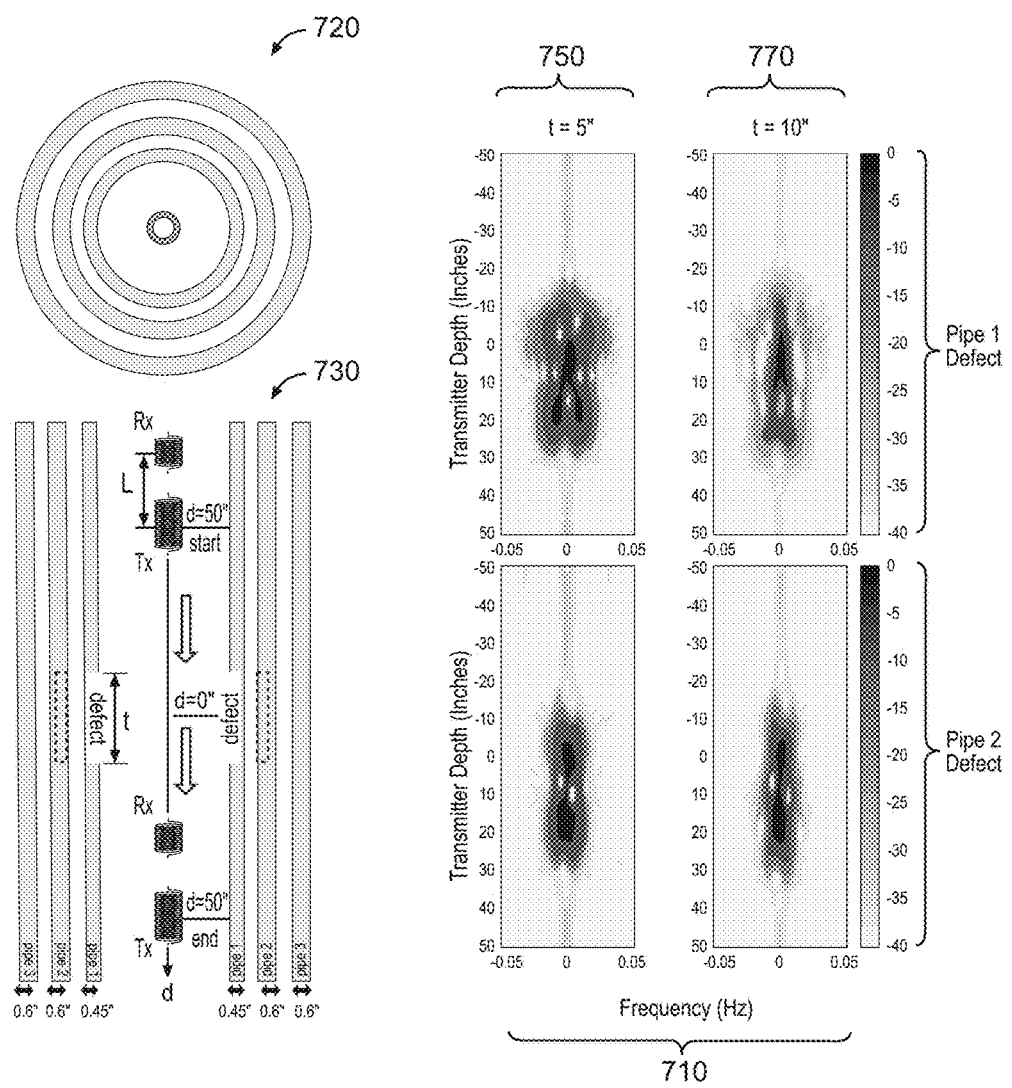
FIG. 7 illustrates time-frequency spectrograms for downhole corrosion simulations with varying pipe defect lengths, according to various embodiments.

FIG. 7 illustrates time-Frequency spectrograms 710 for downhole corrosion simulations with varying pipe defect lengths, according to various embodiments. Again, the shading legend to the right of the spectrograms 710 indicate a vertical scale of decibels (dB) down from a maximum response amplitude (at 0 dB) over the data acquisition cycle for each pipe, and each defect. The horizontal scale for each of the spectrograms is a magnified one, representing a range of plus/minus the sampling rate, divided by two.

The spectrograms 710 give a visual indication (and are useful for machine vision image processing) of known defects in two pipes (i.e., pipe1 and pipe2; shown in a top view 720, and side view 730) to simulate the effects of downhole corrosion. The pipes in this figure are disposed in a concentric arrangement with the series of outside diameters designated OD1.

To obtain the spectrograms 710, a data acquisition frequency of 0.5 Hz, an inspection frequency of 2 Hz, and a transmitter-receiver pair (Tx, Rx) separation distance L=20 inches were used. In this figure, the defect depth is 0.3 inch for both pipes, and the relative permeability of the pipes is also the same: 50.

In this figure, the defect length t changes as the spectrograms 710 are displayed from left to right: the defect length t varies from t=5" in the left set 750 of spectrograms 710, to t=10" in the right set 770 of spectrograms 710. The side view 730 of the pipes shows an explicit defect around the inner perimeter of pipe1, with a defect in dashed-line form for pipe2. These two defects are used to derive the receiver responses, to produce the corresponding spectrograms 710 for each of the pipes pipe1, pipe2 as the transmitter-receiver pair (Tx, Rx) moves over a distance d=−50" to d=+50".

Now that various scenarios have been illustrated, where the effect of changing several inspection parameters can be seen, it becomes apparent that with intelligent processing, a time-frequency spectrogram can be used to determine the extent of defects in piping, to include the effects of corrosion, even when a concentric arrangement of pipes are used. The following discussion will focus on some details that can be inferred from the data presented in conjunction with the prior figures.

FIG. 8 is a table 800 of sensor configurations and pipe parameters for the downhole corrosion simulations of FIGS. 1-7. This is a summary of the changes that have been made to produce the variety of spectrograms in the figures.

Here, two sequences of outer diameters (OD1 and OD2) were selected to cover the range of that is common with commercial piping. In addition, a noise level of 1% (signal-to-noise ratio=40 dB) was included in all simulations. From FIG. 1, it can be seen that voltage response due to a defect in pipe1 exhibits a more pronounced up and down variation across downhole depth than that which occurs for defects in either pipe1 or pipe3. This is because induction tools are more sensitive to conductivity changes at closer radial distances. As the radial distance from the transmitter-receiver pair (Tx, Rx) to the defect increases, vertical resolution decreases, since the high frequency content in the received voltage signal is diminished. Moreover, as electromagnetic fields penetrate more deeply (i.e., radially) into a concentric configuration of pipes, signal response smoothing occurs due to propagation in a medium of higher permeability, further reducing high frequency content in the voltage response waveforms. As a result, it can be useful to consider such smoothing as representing an equivalent signal propagation delay, where the increased pipe permeability makes the apparent radial distance greater. Thus, in some embodiments, these concepts may be used as discriminating factors, to characterize the amount of corrosion with respect to inner and outer pipes in a concentric series of pipes.

To quantitatively demonstrate this intuitive analysis, time-frequency analysis was applied to characterize the frequency content of the simulated voltages at different transmitter depths. Such analysis makes it easier to quantify signal variation (with respect to frequency) as the tool samples receiver response voltages along the axial length of the pipe.

More specifically, a windowing function (e.g., Hamming function) of finite size, centered at a given transmitter depth, was applied to the received voltage signal. A discrete Fourier transform (OFT) was applied to the acquired signal and the process was repeated as the window moved along all transmitter depths at which the received signal was acquired.

This technique, also known as the application of a short-time Fourier transform (STFT), can be used to produce the time-frequency spectrograms shown in FIGS. 1-7. The frequency axis of the spectrogram, depending on the data acquisition (sampling) rate $f_s$, has a range of $[-f_s/2, f_s/2]$. The data acquisition rate $f_s$, is the ratio between logging speed and sample spacing. Here, in these simulations, the spectrogram was generated assuming a data acquisition rate of 0.5 Hz.

In order to observe more clearly any small frequency content near the zero frequency axis, voltage values of the stationary components (i.e., no-defect cases, or piping without defects present) were purposely subtracted from the defect-carrying cases. For example, voltage values of the no-defect cases can be obtained through appropriate time-gating and signal averaging.

A look at the time-frequency spectrogram reveals information about the frequency effect near the region of impact, when the defect is close to the receiver. The width of frequency spread appears to be narrower for outer pipe defects. It should be noted that some remaining amplitude on the zero frequency axis is due to noise. Since all spectrograms are plotted with normalized magnitude, noise appears more strongly when the response levels are diminished, as is the case for defects in the outermost pipes in a concentric series, such as pipe3 in the figures.

To understand how other configurations and pipe parameters affect frequency spread, FIGS. 2-5 display the time-frequency spectrograms with varying defect depth, pipe permeability, inspection frequencies, transmitter-receiver (Tx, Rx) spacing, and pipe outer diameters, respectively. As shown in these figures, frequency spread remains relatively unchanged for variations in defect thickness, transmitter-receiver spacing, and frequency; it appears to be affected more by the radial distance between the defect and the receiver Rx. Taking physics into account, it might be expected that defect size, transmitter-receiver (Tx, Rx) spacing, and inspection frequency would affect the magnitude of the received voltage, but in the surprising result discovered herein, the frequency content of the received voltage signal is only slight altered.

Moreover, it may be noted that in FIG. 5, pipe2 in the OD1 arrangement is in the same radial position as pipe1 of the OD2 arrangement. Similarly, pipe3 in the OD1 arrangement has the same radial position as pipe2 in the OD2 arrangement. Close examination of FIGS. 1 and 5 shows a similar frequency spread for defects at the same radial distance, but when the signal penetrates an extra pipe, the aforementioned smoothing effect accounts for the minor difference between the two situations. This same smoothing affect is also observed in FIG. 3 for increasing pipe permeability, where the incoming signal waveform slows down, making the radial distance between the receiver Rx and the defect appear longer, via the narrowed width of the frequency spread.

Thus, it can be concluded that the width of frequency spread decreases with a longer radial distance and greater pipe penetration. This means that the frequency spread can be used as a measure the defect radial position, to distinguish the presence of a defect in pipe1, pipe2, or pipe3 (as well as other pipes in a concentric series) for any given set of piping outer diameters.

To quantify this relationship in mathematical terms, the width of Frequency spread ($W_{spread}$) may be approximately inversely proportional to the defect's apparent radial position $r_{app}$, defined in Equation (1) as:

$$r_{app} \cong r_{geometric} + (\sqrt{\mu_r} - 1)t_{pipe} \qquad (1)$$

where $r_{geometric}$ is the actual radial position of the defect, $\mu_r$ is the relative permeability of the pipe, and $t_{pipe}$ is the total thickness of metal (cumulative thickness of multiple pipes in a concentric series) which the transmitter Tx EM field penetrates. In some embodiments, the transmitter Tx may comprise a time-harmonic eddy current transmitter.

The first term of the right hand side of Equation (1) represents the signal impact due to defect's actual radial position while the second term represents the signal impact due to pipe penetration. Because the outside diameter of a pipe is generally much larger than the pipe wall thicknesses (i.e., $r_{geometric} \gg t_{pipe}$), the first term of Equation (1) dominates the right hand side of the equation unless the pipe permeability, not uncommon in magnetic steel, or thickness, is large. Therefore, for any given set of concentric pipes, a defect on the outer pipe (e.g., pipe2 or pipe3) should have a noticeably smaller frequency spread than a defect on an inner pipe (e.g., pipe1), since a defect on an outer pipe not only has a greater radial distance, but the EM waves from the transmitter Tx have to penetrate a greater number of pipes.

To extract information after a spectrogram has been generated, an image segmentation algorithm with appropriate level thresholds can be applied. In this manner, the width of frequency spread can be extracted automatically. The approximation described by Equation (1) can be improved by constructing a database of relationships between defect radial position in a concentric piping configuration, and frequency spread. The database can be used in conjunction with image comparison algorithms to determine a correlation between acquired data and information in the database.

In order to obtain responses from pipes that are (radially) farther away from the receiver in a concentric configuration, low frequencies (e.g., approximately 2-10 Hz) can be chosen, to provide a greater skin depth δ, defined in Equation (2) as:

$$\delta = \sqrt{2/\sigma\mu\omega} \quad (2)$$

where σ is the electrical conductivity, and μ is the magnetic permeability of the pipes in the configuration, and ω is the angular frequency of inspection.

FIGS. 6-7 illustrate how changes in transmitter-receiver (Tx, Rx) spacing and defect size affect the spectrogram presentation. As can be seen in these figures, the span of non-zero frequency spread, referred to herein as the "region of impact", begins precisely when the transmitter first begins to have an axial overlap with the defect, and ends precisely when the receiver and the defect no longer have any axial overlap. If $L_T$, $L_R$, and $L_{ROI}$ are the length of the transmitter, the length of the receiver, and the length of the region of impact, respectively, then for a given transmitter-receiver (Tx, Rx) spacing L, the defect size t may be estimated as shown in Equation (3):

$$t \sim L_{ROI} - \left(L + \frac{L_T + L_R}{2}\right). \quad (3)$$

This formula is validated by the spectrograms 710 shown in FIG. 7. That is, viewing the non-zero frequency region within 10 dB of the maximum magnitude at 0 dB for the case of a 5" defect length reveals an impact region $L_{ROI}$ span of approximately 30-33", which is consistent with a distance of 31" that is calculated from Equation (3). The same consistency is found when a 10" defect length is used for the pipe1 defect.

In practice, the same image processing algorithms used to automatically extract the width of the frequency spread may also be applied to estimate the length of the impact region $L_{ROI}$. Having estimated the spread and length of non-zero frequency content allows knowledge to be gained concerning the location and extent of corrosion in pipes. The approximation described by Equation (3) can also be improved by constructing a database of defects as part of different concentric piping configurations, where relationships between defect size, transmitter-receiver pair (Tx, Rx) separation, and the distance between the defect and the receiver Rx can be quantified and maintained for comparison with the measured length of the region of impact. In some embodiments, spectrograms are constructed and analyzed in real-time, to provide ongoing indications of piping integrity.

Thus, in some embodiments, a database is be constructed in order to determine the radial distance of a defect (from the receiver Rx), and its size. For this purpose, a database can be constructed by producing spectrograms for pipes with various outside diameters. This corresponds with the assumption that the effect of the second term in Equation (1) is negligible in most cases (i.e., that the permeability or thickness of the pipes have a relatively small effect). The spectrograms can be produced for a fixed defect size, number of turns in a receiver coil, core properties and dimensions of the transmitter, and the relative spacing between the transmitter and receiver components in the transmitter-receiver (Tx, Rx) pair, over a number of inspection frequencies.

Since the logging speed has some effect on the sampling frequency, normalization with respect to the sampling frequency can be applied when creating the database. Thus, for any measurements made with arbitrary logging speed, normalization of sampling frequency will can be applied prior to comparing acquired spectrogram images with those stored in the database. If the effect of the second term in Equation (1) is deemed not to be negligible (i.e., the permeability or thickness of the pipes has a relatively large effect on the result), then a database can be created over a variety of permeability and wall thickness dimensions, as well as other properties of the pipes.

In order to evaluate the defects on the pipes in a concentric pipe inspection scenario, several approaches can be implemented. For example, in a first approach, the average width can be computed for the images of spectrograms in the database, and compared to the average width of the spectrogram obtained from the measurement. In order to compute the average width of an individual spectrogram, the image can be converted to a contour showing the variations of the spectrogram due to the defect, and then the average width of the largest contour can be computed. The average width computed from the measured spectrogram is then compared with those in the database to determine the approximate radial distance to the defect, and thus, which pipe in a concentric series contains the defect.

Although the depth of the defect region is difficult to estimate using this approach, the defect length along the axial direction can be estimated by considering the extent of the largest contour along the axial direction, the length of the transmitter, the length of the receiver, and the transmitter-receiver pair (Tx, Rx) spacing, according to Equation (3).

In a second approach, the spectrogram obtained from the measurement ($S^{mes}$) can be compared with the spectrograms in the database ($S^{database}$), to find the closest match. A cost function J can be computed to accomplish this task, based on the difference between $S^{mes}$ and $S^{database}$, as shown for Equation (4):

$$J = \|S^{mes} - S^{database}\| \quad (4)$$

where $\|.\|$ may comprise the 2-norm operator in some embodiments.

During the inversion process an attempt is made to minimize J that leads to defect characterization. The cost function J can be constructed using more complicated pattern matching techniques—such as by computing the mathematical correlation between $S^{mes}$ and $S^{database}$ in an attempt to find the database spectrogram $S^{database}$ that has the highest correlation with the measured spectrogram $S^{mes}$. Thus, many embodiments may be realized.

Figure 9:
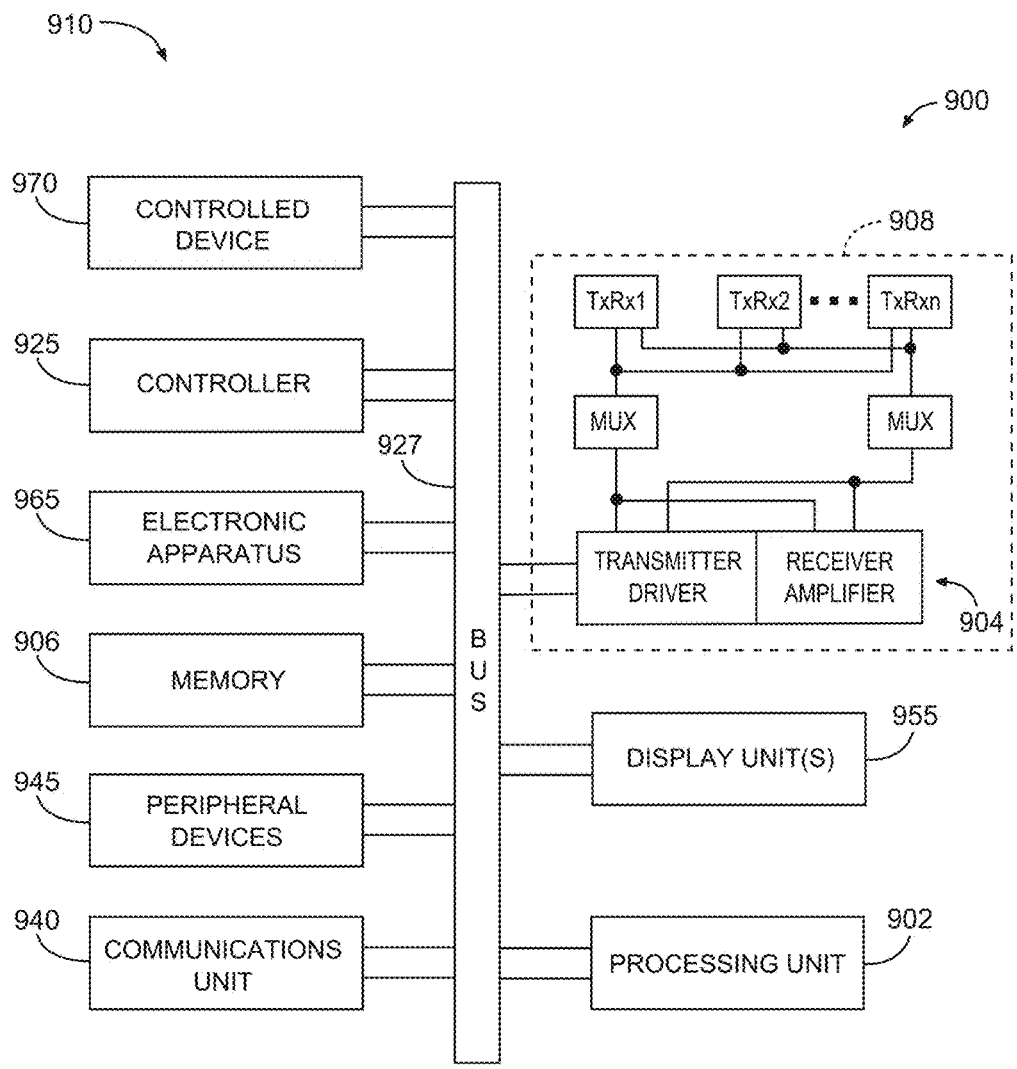
FIG. 9 is a block diagram of a logging system according to various embodiments.

For example, FIG. 9 is a block diagram of a logging system 910 according to various embodiments. Referring now to FIGS. 1 and 9, it can be seen that the logging system 910 can receive measurement data from the receivers Rx1, Rx2, . . . , Rxn located in or on a housing 908, forming part of an apparatus 900. The transmitters Tx1, Tx2, . . . , Txn and the receivers Rx1, Rx2, . . . , Rxn may each be located in or on the housing 908, and may be operated in conjunction with transmitter driver(s) and receiver amplifier(s) 904 attached to the housing 908, forming part of the apparatus 900, or forming part of a controlled device 970.

In either case, the transmitter driver(s) 904 can be used to energize the transmitters Tx1, Tx2, . . . , Txn (which may comprise one or more time-harmonic eddy current transmitters) to transfer electromagnetic energy into the surrounding pipes, to produce eddy currents. The receivers Rx1, Rx2, . . . , Rxn can be coupled to the receiver amplifier(s) 904) to make measurements of the resulting response voltages. The logging system 910 thus may include one or more transmitter-receiver pairs (Tx, Rx) operating in a wellbore.

The processing unit 902 can couple to the apparatus 900 to obtain measurements from the transmitter-receiver pairs (Tx, Rx) and other devices as described earlier herein. In some embodiments, a logging system 910 comprises one or more of the transmitter-receiver pairs (Tx, Rx), as well as a housing 908 (see also FIGS. 11-12) that forms part of the apparatus 900. The housing might take the form of a wireline tool body, or a downhole tool as described in more detail below with reference to FIGS. 11 and 12. The processing unit 902 may be part of a surface workstation or attached to a downhole tool housing. In some embodiments, the processing unit 902 may be packaged within the housing 908.

The logging system 910 can include a controller 925, other electronic apparatus 965, and a communications unit 940. The controller 925 and the processing unit 902 can be fabricated to operate the apparatus 900 to acquire measurement data, such as signals corresponding to eddy current measurements.

Electronic apparatus 965 (e.g., electromagnetic sensors, etc.) can be used in conjunction with the controller 925 to perform tasks associated with taking measurements downhole, using the apparatus 900. The communications unit 940 can include downhole communications in a wireline or drilling operation. Such downhole communications can include a telemetry system.

The logging system 910 can also include a bus 927 to provide common electrical signal paths between the components of the logging system 910. The bus 927 can include an address bus, a data bus, and a control bus, each independently configured. The bus 927 can also use common conductive lines for providing one or more of address, data, or control, the use of which can be regulated by the controller 925.

The bus 927 can include instrumentality for a communication network. The bus 927 can be configured such that the components of the logging system 910 are distributed. Such distribution can be arranged between downhole components such as the measurement device 904 and components that can be disposed on the surface of a well. Alternatively, several of these components can be co-located such as on one or more collars of a drill string or on a wireline structure.

In various embodiments, the logging system 910 includes peripheral devices 945 that can include displays 955, additional storage memory, or other controlled devices 970 that may operate in conjunction with the controller 925 or the processing unit 902. The display 955 can display diagnostic information for the apparatus 900 based on the measurements made according to various embodiments described above. The display 955 can also be used to display one or more graphs, similar to or identical to the received voltages and corresponding spectrograms illustrated in FIGS. 1-7.

In an embodiment, the controller 925 can be fabricated to include one or more processors. The display 955 can be fabricated or programmed to operate with instructions stored in the processing unit 902 (for example in the memory 906) to implement a user interface to manage the operation of the apparatus 900 or components distributed within the logging system 910. This type of user interface can be operated in conjunction with the communications unit 940 and the bus 927. Various components of the logging system 910 can be integrated with the apparatus 900 and an associated housing 908 such that processing identical to or similar to the methods discussed with respect to various embodiments herein can be performed downhole. Thus, any one or more components of the apparatus 900 and/or controlled device 970 may be attached to or contained within the housing 908.

In various embodiments, a non-transitory machine-readable storage device can comprise instructions stored thereon, which, when performed by a machine, cause the machine to become a customized, particular machine that performs operations comprising one or more features similar to or identical to those described with respect to the methods and techniques described herein. A machine-readable storage device, herein, is a physical device that stores information (e.g., instructions, data), which when stored, alters the physical structure of the device. Examples of machine-readable storage devices can include, but are not limited to, memory 906 in the form of read only memory (ROM), random access memory (RAM), a magnetic disk storage device, an optical storage device, a flash memory, and other electronic, magnetic, or optical memory devices, including combinations thereof.

The physical structure of stored instructions may be operated on by one or more processors such as, for example, the processing unit 902. Operating on these physical structures can cause the machine to perform operations according to methods described herein. The instructions can include instructions to cause the processing unit 902 to store measurement data, databases (e.g., generated according to methods described herein), and other data in the memory 906. The memory 906 can store the results of measurements of piping condition, as well as gain parameters, calibration constants, identification data, etc. The memory 906 therefore may include one or more databases, such as a relational database.

Figure 10:
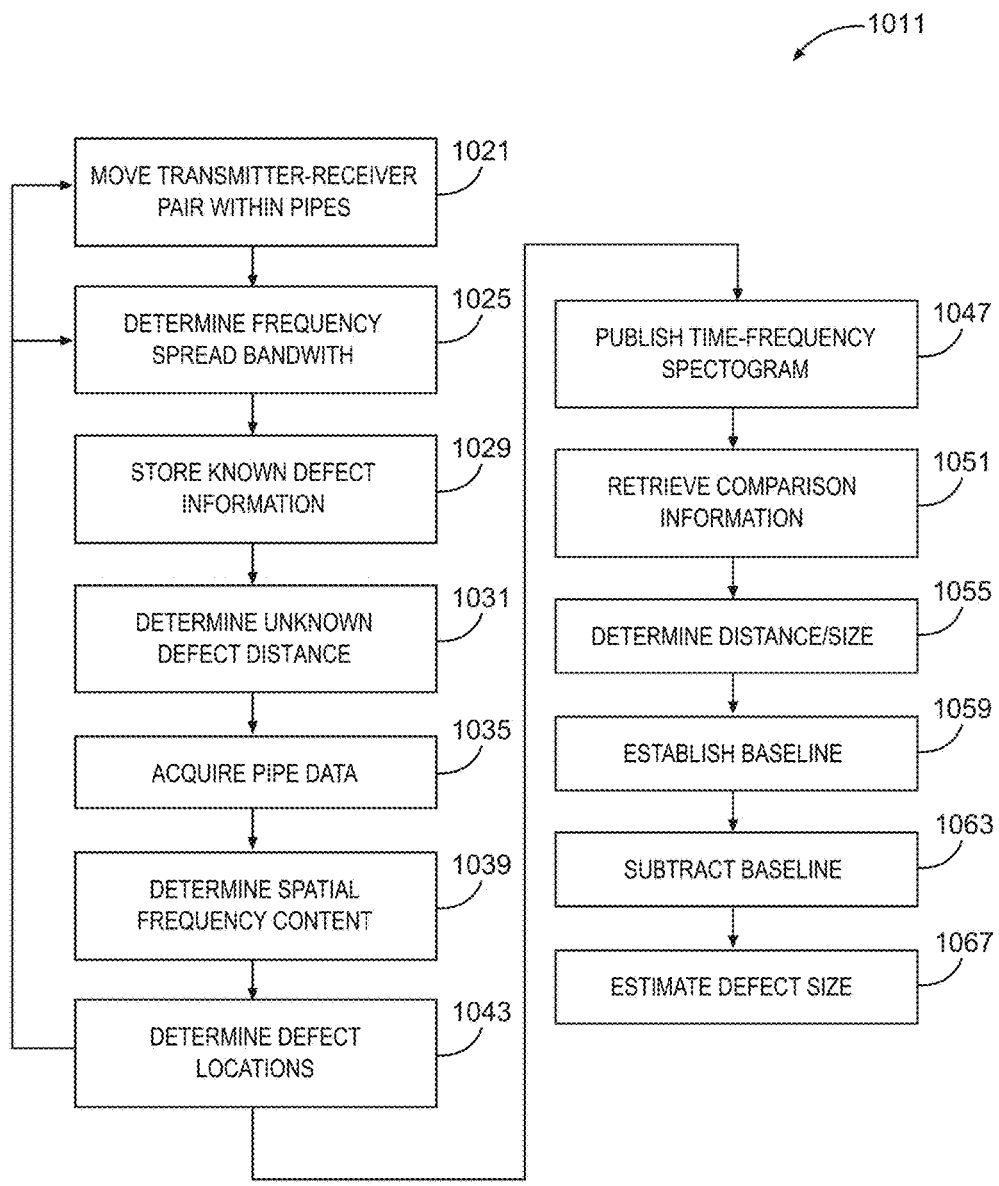
FIG. 10 is a flow diagram illustrating methods of determining pipe defect locations and size, according to various embodiments.

FIG. 10 is a flow diagram illustrating methods 1011 of determining pipe defect locations and size, according to various embodiments. To begin, methods of database construction to build a database in memory for comparison with known defects will be described. These methods may operate to enable dynamic comparison of the database information with measurement data, to effect the control of various devices in a logging while drilling or wireline logging environment.

In some embodiments, a method 1011 begins at block 1021 with moving a transmitter-receiver pair within a first group of concentric pipes to acquire known defect eddy current data. The method 1011 may continue on to include determining a frequency spread bandwidth associated with the known defect eddy current data and known defects in the first group of concentric pipes at block 1025.

In some embodiments, the method 1011 may continue on to block 1029 to include storing sizes of the known defects and associated values of the frequency spread bandwidth, or values derived from the frequency spread bandwidth, as known defect information in a memory, to enable determination of unknown defect size in a second group of concentric pipes, which may be disposed in a geological formation. This determination can be made upon access to and comparison with signals received by an inspection transmitter-receiver pair disposed in the second group of concentric pipes.

Other determinations can be made. For example, the radial distance to an unknown defect can be determined, based on comparison with information in the memory. Thus, in some embodiments, the method 1011 may include determining a radial distance of at least one unknown defect associated with the unknown defect size based on the known defect information, at block 1031.

A cost function can be used to determine how well information stored in the memory compares with acquired eddy current data. Thus, in some embodiments, determining the radial distance at block 1031 comprises comparing spectrograms to minimize a cost function.

In some embodiments, a method 1011 of determining pipe defect locations begins at block 1035 with acquiring data, and continues on to block 1039 to determine spatial frequency content. In some embodiments, the method 1011 includes determining defect location(s) based on the spatial frequency content at block 1043.

In some embodiments the method 1011 begins with blocks 1021, 1025, and 1029 to build a database that includes known defect information. The method 1011 continues on to block 1035 to include acquiring eddy current data from at least two concentric pipes. In this and other embodiments, the concentric pipes may comprise groups of piping found in hydrocarbon extraction facilities. Thus, in some embodiments, the concentric pipes may comprise at least one production pipe, at least one completion pipe, or a casing, or any combination of these.

In some embodiments, the method 1011 includes, at block 1039, determining the spatial frequency content of the eddy current data acquired at block 1035, and then continues on to include, at block 1043, determining locations of defects in each of the pipes, based on the spatial frequency content determined at block 1039.

Defect location can include the radial distance of the defect from a centerline of receiver Rx travel, and/or the azimuthal location of the defect. Thus, the activity of determining the locations of the defects at block 1043 may further comprise determining the radial distance and azimuthal location of the defects.

The radial distance of a defect can be determined using pipe permeability. Thus, the activity of determining the radial distance may be based on relative permeability of at least one of the concentric pipes.

Spectrograms derived from the data can be published in human-readable form. Thus, in some embodiments, the method 1011 comprises, at block 1047, publishing a time-frequency spectrogram derived from the eddy current data in a human-readable format, using shading or color to indicate relative signal strength. The technique of shading is shown explicitly in FIGS. 1-7, while the application of color may be accomplished by substituting hues of the rainbow, for example, for various shades of gray used in the illustrations of the spectrograms.

Comparisons between spectrograms can be used to determine characteristics of the defects. Thus, in some embodiments, the method 1011 includes, at block 1051, retrieving information from a memory to form a comparison between the information and a time-frequency spectrogram derived from the eddy current data. In some embodiments, the method 1011 continues on to block 1055 to include determining at least one of a radial distance or a size associated with one or more of the defects, based on the comparison.

The acquired data may be refined, perhaps to remove noise, by subtracting known good signal data. Thus, some embodiments of the method 1011 may include, at block 1059, establishing a baseline signal response for the eddy current data by at least one of scanning a section of pipe without defects or accessing a database that includes baseline data for the concentric pipes. The method 1011 may continue on to block 1063, to include subtracting the baseline signal response from the eddy current data to preprocess the eddy current data.

The size of a defect can be estimated, using the distance traveled by a transmitter-receiver pair. Thus, some embodiments of the method 1011 include, at block 1067, estimating the size of at least one of the defects based on a travel distance of a transmitter and a receiver.

The size of a defect can be estimated, using the regions of impact for a transmitter-receiver pair, which may or may not equate to the distance traveled, depending on the frequency of excitation, and the strength of the excitation signal. Thus, the activity at block 1067 may comprise estimating the size of at least one of the defects based on a region of impact for a transmitter-receiver pair that is used to acquire the eddy current data. Still further embodiments may be realized.

Figure 11:
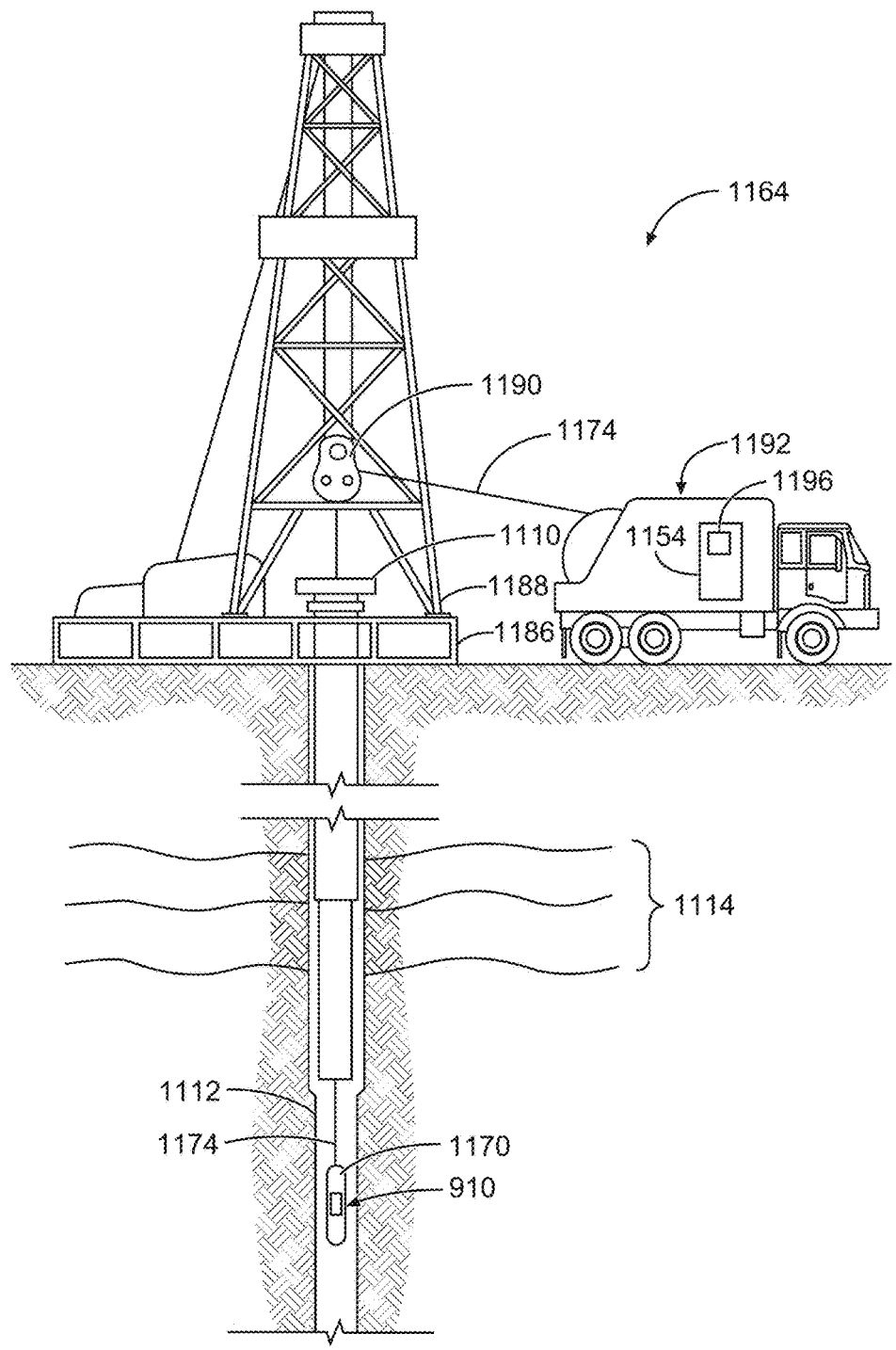
FIG. 11 depicts an example slickline/wireline system, according to various embodiments.
Figure 12:
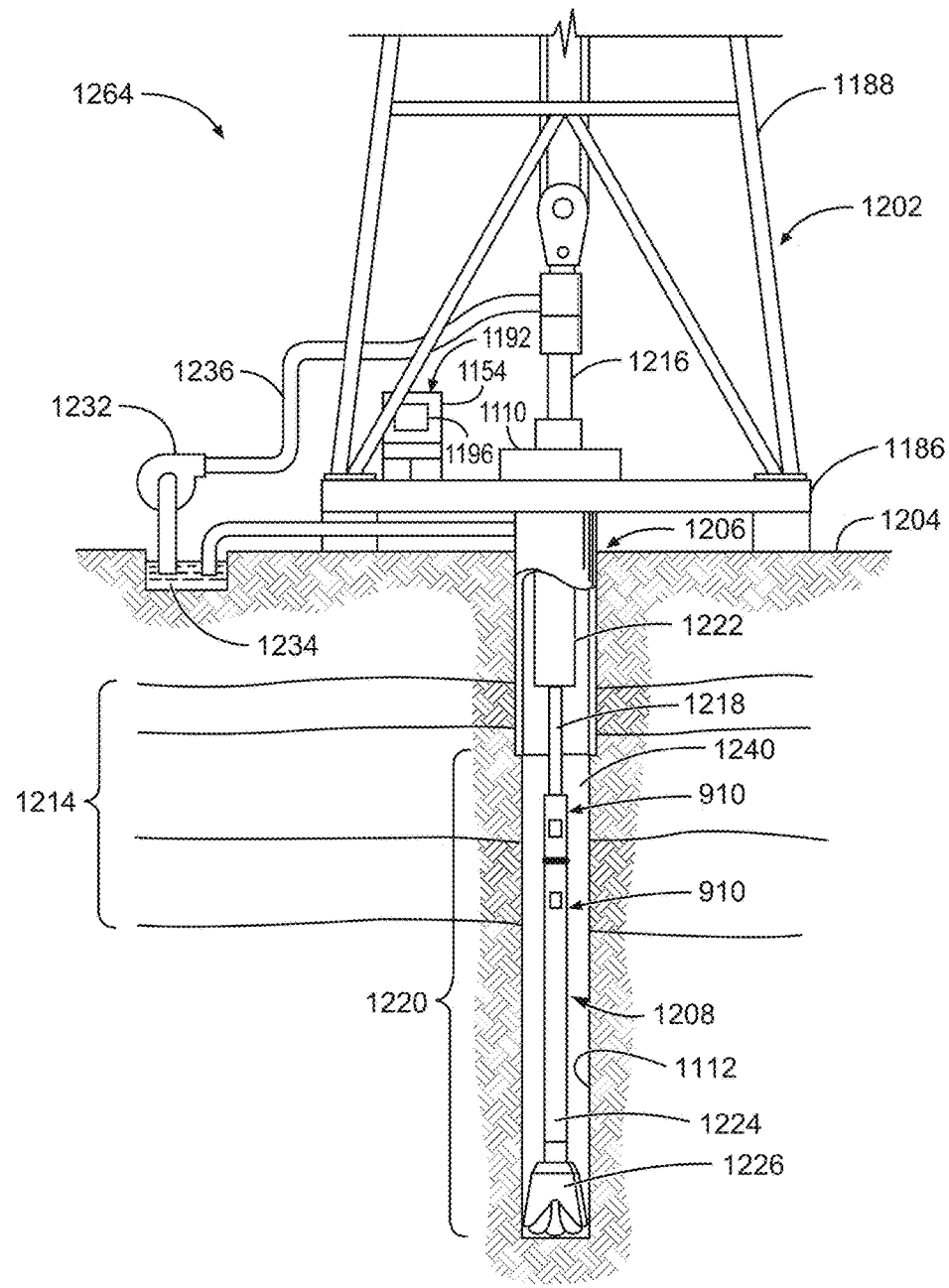
FIG. 12 depicts an example drilling rig system, according to various embodiments.

For example, FIG. 11 depicts an example slickline/wireline system 1164, according to various embodiments. FIG. 12 depicts an example drilling rig system 1264, according to various embodiments. Either of the systems in FIGS. 11 and 12 are operable to control the apparatus 900 or system 910 (see FIG. 9) to conduct measurements in a wellbore. Thus, the systems 1164, 1264 may comprise portions of a tool body 1170 as part of a slickline or wireline logging operation, or of a downhole tool 1224 (e.g., a drilling operations tool) as part of a downhole drilling operation.

Returning now to FIG. 11, a well during wireline logging operations can be seen. In this case, a drilling platform 1186 is equipped with a derrick 1188 that supports a hoist 1190.

Drilling oil and gas wells is commonly carried out using a string of drill pipes connected together so as to form a drilling string that is lowered through a rotary table 1110 into a wellbore or borehole 1112. Here it is assumed that the drilling string has been temporarily removed from the borehole 1112 to allow a tool body 1170, such as a probe or sonde, to be lowered by slickline, wireline, or logging cable 1174 into the borehole 1112. Thus, in some embodiments, the systems 1164 may implement the tool body 1170 as a slickline tool housing, or as a wireline tool housing. In any case, the tool body 1170 may be lowered to the bottom of the region of interest and subsequently pulled upward at a substantially constant speed.

During the upward trip, at a series of depths the instruments (e.g., the receivers Rx of system 910 shown in FIG. 9) included in the tool body 1170 may be used to perform measurements on the subsurface geological formations adjacent the borehole 1112 (and the tool body 1170). The measurement data can be communicated to a surface logging facility 1192 for storage, processing, and analysis. The logging facility 1192 may be provided with electronic equipment for various types of signal processing, which may be implemented by any one or more of the components of the system 910 and/or a display 1196 to view the results. Similar piping evaluation data may be gathered and analyzed during drilling operations (e.g., during) operations, and by extension, sampling while drilling).

In some embodiments, the tool body 1170 comprises one or more transmitter-receiver pairs (Tx, Rx) for obtaining and analyzing eddy current measurements in piping disposed in a borehole 1112. The tool is suspended in the wellbore by a cable 1174 that connects the tool to a surface control unit (e.g., comprising a workstation 1154, which can also include a display). The tool may be deployed in the borehole 1112 on coiled tubing, jointed drill pipe, hard wired drill pipe, or any other suitable deployment technique.

Turning now to FIG. 12, it can be seen how a system 1264 may also form a portion of a drilling rig 1202 located at the surface 1204 of a well 1206. The drilling rig 1202 may provide support for a drill string 1208. The drill string 1208 may operate to penetrate the rotary table 1110 for drilling the borehole 1112 through the subsurface formations 1114. The drill string 1208 may include a Kelly 1216, drill pipe 1218, and a bottom hole assembly 1220, perhaps located at the lower portion of the drill pipe 1218.

The bottom hole assembly 1220 may include drill collars 1222, a downhole tool 1224, and a drill bit 1226. The drill bit 1226 may operate to create the borehole 1112 by penetrating the surface 1204 and the subsurface formations 1214. The downhole tool 1224 may comprise any of a number of different types of tools including MWD tools, LWD tools, and others.

During drilling operations, the drill string 1208 (perhaps including the Kelly 1216, the drill pipe 1218, and the bottom hole assembly 1220) may be rotated by the rotary table 1110. Although not shown, in addition to, or alternatively, the bottom hole assembly 1220 may also be rotated by a motor (e.g., a mud motor) that is located downhole. The drill collars 1222 may be used to add weight to the drill bit 1226. The drill collars 1222 may also operate to stiffen the bottom hole assembly 1220, allowing the bottom hole assembly 1220 to transfer the added weight to the drill bit 1226, and in turn, to assist the drill bit 1226 in penetrating the surface 1204 and subsurface formations 1214.

During drilling operations, a mud pump 1232 may pump drilling fluid (sometimes known by those of ordinary skill in the art as "drilling mud") from a mud pit 1234 through a hose 1236 into the drill pipe 1218 and down to the drill bit 1226. The drilling fluid can flow out from the drill bit 1226 and be returned to the surface 1204 through an annular area 1240 between the drill pipe 1218 and the sides of the borehole 1112. The drilling fluid may then be returned to the mud pit 1234, where such fluid is filtered. In some embodiments, the drilling fluid can be used to cool the drill bit 1226, as well as to provide lubrication for the drill bit 1226 during drilling operations. Additionally, the drilling fluid may be used to remove subsurface formation cuttings created by operating the drill bit 1226.

Thus, it may be seen that in some embodiments, the systems 1164, 1264 may include a drill collar 1222, a downhole tool 1224, and/or a slickline or wireline logging tool body 1170 to house one or more components of the system 910 in FIG. 9.

Thus, for the purposes of this document, the term "housing" may include any one or more of a drill collar 1222, a downhole tool 1224, or a tool body 1170 (all having an outer wall, to enclose or attach to magnetometers, sensors, fluid sampling devices, pressure measurement devices, transmitters, receivers, acquisition and processing logic, and data acquisition systems). The tool 1224 may comprise a downhole tool, such as an LWD tool or MWD tool. The tool body 1170 may comprise a wireline logging tool, including a probe or sonde, for example, coupled to a wireline cable 1174, or a slickline tool body coupled to a slickline cable 1174. Many embodiments may thus be realized.

For example, a system 1164, 1264 may comprise a downhole tool body, such as a slickline or wireline logging tool body 1170 or a downhole tool 1224 (e.g., an LWD or MWD tool body), and one or more transmitter-receiver pairs (Tx, Rx) attached to the tool body.

Thus referring to FIGS. 1, 9, and 11-12, it can be seen that in some embodiments a system 910 comprises a transmitter-receiver pair (Tx, Rx), and a controller 925 to operate the pair, to acquire eddy current data and determine defect locations based on spatial frequency content of the acquired data.

In some embodiments, a system 910 comprises at least a transmitter and a receiver (Tx, Rx), movable to occupy a range of depths within an inner diameter of at least two concentric pipes (e.g., pipe1, pipe2) disposed in a geological formation. The a system 910 may further comprise a controller 925 to drive the transmitter Tx to excite eddy currents in the pipes, to acquire corresponding eddy current data from the receiver Rx, and to determine locations of defects in each of the pipes based on spatial frequency content of the eddy current data. The transmitter Tx may comprise an eddy current transmitter, including a time-harmonic eddy current transmitter.

The transmitter-receiver pair (Tx, Rx) may be attached to a common housing 908. Thus, in some embodiments, the transmitter and the receiver (Tx, Rx) are attached to a common housing 908, and separated by an axial distance L along the housing 908.

The housing 908 may comprise any number of devices. Thus, in some embodiments, the housing 908 comprises one of a slickline tool housing, a wireline tool housing, or a drill string tool housing.

The system 910 may include a memory 906 to store a database. Thus, some embodiments of a system 910 comprise a memory 906 accessible by the controller 925, the memory 906 to store a database comprising predetermined relationships between a set of radial distance values associated with the locations of the defects, and a set of frequency spread bandwidth values.

The a system 910 may comprise a display 955 to exhibit spectrograms in real time, which for the purposes of this document means publishing a spectrogram in human readable format within one minute after the data is acquired downhole. The display 955 may thus be coupled to the controller 925, to publish time-frequency spectrograms derived from the eddy current data in substantially real time.

The controller 925 may operate to normalize the eddy current data. Thus, in some embodiments, the controller 925 operates to normalize the eddy current data according to a logging speed of the receiver Rx, to provide normalized eddy current data.

Normalized data can be compared to determine defect size. Thus, in some embodiments, the controller 925 operates to compare the normalized eddy current data, or normalized spectrograms derived from the normalized eddy current data, with spectrograms stored in a memory 906 and associated with defects of a known size and radial distance.

Any of the above components, for example the transmitter-receiver pair(s) (Tx, Rx), or the systems 910, 1164, 1264 (and each of their elements) may be characterized as "modules" herein. Such modules may include hardware circuitry, and/or a processor and/or memory circuits, software program modules and objects, and/or firmware, and combinations thereof, as desired by the architect of the systems 910, 1164, 1264 and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, a measured radiation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of systems 910, 1164, 1264 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules.

It should be noted that the methods described herein at FIG. 10 do not have to be executed in the order described, or in any particular order. Moreover, various activities described with respect to the methods identified herein can be executed in iterative, serial, or parallel fashion. Activities in one method may be substituted for those of another method. Information, including parameters, commands, operands, and other data, can be sent and received in the form of one or more carrier waves.

Many more embodiments can be realized. Some of these will now be listed as non-limiting examples.

In some embodiments, a system comprises at least a transmitter and a receiver, movable to occupy a range of depths within an inner diameter of at least two concentric pipes disposed in a geological formation. Thus, multiple transmitters and multiple receivers may be included in the system.

In some embodiments, the system includes a controller to drive a transmitter to excite eddy currents in concentric arrangements of pipes, to acquire corresponding eddy current data from a receiver, and to determine locations of defects in each of the pipes based on spatial frequency content of the eddy current data.

In some embodiments, the system comprises one or more transmitters, which in turn comprise an eddy current transmitter, such as a time-harmonic eddy current transmitter.

In some embodiments, the system comprises a transmitter and receiver attached to a common housing, and separated by an axial distance along the housing. In some embodiments, the housing comprises one of a slickline tool housing, a wireline tool housing, or a drill string tool housing.

In some embodiments, a system comprises a memory accessible by a controller, the memory to store a database comprising predetermined relationships between a set of radial distance values associated with the locations of defects, and a set of frequency spread bandwidth values.

In some embodiments, a system comprises a display coupled to a controller, the display to publish time-frequency spectrograms derived from eddy current data in substantially real time.

In some embodiments, a system comprises a controller to normalize eddy current data according to a logging speed of a receiver, to provide normalized eddy current data.

In some embodiments, a system comprises a controller to compare normalized eddy current data, or normalized spectrograms derived from normalized eddy current data, with spectrograms stored in a memory and associated with defects of a known size and radial distance.

Some embodiments comprise a method. Such methods may comprise acquiring eddy current data from at least two concentric pipes; determining spatial frequency content of the eddy current data; and determining locations of defects in each of the pipes based on the spatial frequency content. In some embodiments, the concentric pipes comprise at least one production pipe, at least one completion pipe, and/or a casing, or some combination of these.

In some embodiments, a method comprises publishing a time-frequency spectrogram derived from eddy current data in a human-readable format, using shading or color to indicate relative signal strength.

In some embodiments, a method comprises retrieving information from a memory to form a comparison between the information and a time-frequency spectrogram derived from eddy current data; and determining at least one of a radial distance or a size associated with one or more of the defects, based on the comparison.

In some embodiments, a method comprises establishing a baseline signal response for eddy current data by at least one of scanning of a section of pipe without defects or accessing a database that includes baseline data for the concentric pipes; and subtracting the baseline signal response from the eddy current data to pre-process the eddy current data.

In some embodiments, determining locations of defects comprises determining a radial distance and azimuthal location of the defects.

In some embodiments, a method comprises determining a radial distance to a defect based on relative permeability of at least one of several concentric pipes.

In some embodiments, a method comprises estimating the size of at least one of the defects based on a travel distance of a transmitter and a receiver. In some embodiments, a method comprises estimating a size of at least one of the defects based on a region of impact for a transmitter-receiver pair that is used to acquire the eddy current data.

In some embodiments, a method comprises moving a transmitter-receiver pair within a first group of concentric pipes to acquire known defect eddy current data; determining a frequency spread bandwidth associated with the known defect eddy current data and known defects in the first group of concentric pipes; and storing sizes of the known defects and associated values of the frequency spread bandwidth, or values derived from the frequency spread bandwidth, as known defect information in a memory, to enable determination of unknown defect size in a second group of concentric pipes disposed in a geological formation upon access to and comparison with signals received by an inspection transmitter-receiver pair disposed in the second group.

In some embodiments, a method comprises determining a radial distance of at least one unknown defect associated with the unknown defect size based on known defect information. In some embodiments, determining the radial distance comprises comparing spectrograms to minimize a cost function.

Some embodiments are realized as a system. Thus, in some embodiments, a system 1164, 1264 comprises a housing 908 which includes any one or more of the components of the apparatus 900 and/or the system 910.

In summary, using the apparatus, systems, and methods disclosed herein utilizes time-frequency spectrogram signatures to inspect and/or monitor casing integrity. The techniques can be applied to many sizes of pipe and casing, at a variety of inspection frequencies, and in real time. Image processing can be used to automatically characterize defects. As a result, more consistent and accurate assessment of downhole conditions is available, providing increased customer satisfaction.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein. For example, the programs may be structured in an object-orientated format using an object-oriented language such as Java or C. In another example, the programs can be structured in a procedure-orientated format using a procedural language, such as assembly or C. The software components may communicate using any of a number of mechanisms well known to those of ordinary skill in the art, such as application program interfaces or interprocess communication techniques, including remote procedure calls. The teachings of various embodiments are not limited to any particular programming language or environment.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Although specific embodiments have been illustrated and described herein, it will be appreciated by those of ordinary skill in the art that any arrangement that is calculated to achieve the same purpose may be substituted for the specific embodiments shown. Various embodiments use permutations or combinations of embodiments described herein. It is to be understood that the above description is intended to be illustrative, and not restrictive, and that the phraseology or terminology employed herein is for the purpose of description. Combinations of the above embodiments and other embodiments will be apparent to those of ordinary skill in the art upon studying the above description.

What is claimed is:

1. A system, comprising:
    at least a transmitter and a receiver, movable to occupy a range of depths within an inner diameter of at least two concentric pipes disposed in a geological formation; and
    a controller configured to drive the transmitter to excite eddy currents in the pipes, to acquire corresponding eddy current data from the receiver, and to determine locations of defects in each of the pipes based on spatial frequency content of the eddy current data;
    wherein the controller is further configured to compare the eddy current data with spectrograms stored in a memory and associated with defects of a known size and radial distance to determine the locations of defects.

2. The system according to claim 1, wherein the transmitter comprises a time-harmonic eddy current transmitter.

3. The system according to claim 1, wherein the transmitter and the receiver are attached to a common housing, and separated by an axial distance along the housing.

4. The system according to claim 3, wherein the housing comprises one of a slickline tool housing, a wireline tool housing, or a drill string tool housing.

5. The system according to claim 1, further comprising:
    the memory accessible by the controller, the memory to store a database comprising predetermined relationships between a set of radial distance values associated with the locations of the defects, and a set of frequency spread bandwidth values.

6. The system according to claim 1, further comprising:
    a display coupled to the controller, the display to publish time-frequency spectrograms derived from the eddy current data in substantially real time.

7. The system according to claim 1, wherein the controller is configured to normalize the eddy current data according to a logging speed of the receiver, to provide normalized eddy current data.

8. The system of claim 7, wherein the controller is configured to compare the normalized eddy current data, or normalized spectrograms derived from the normalized eddy current data, with spectrograms stored in the memory and associated with defects of the known size and radial distance.

9. A method comprising:
    moving a transmitter-receiver pair within at least two concentric pipes;
    driving the transmitter to excite eddy currents within the at least two concentric pipes;
    acquiring, by the receiver, eddy current data from the at least two concentric pipes;
    determining spatial frequency content of the eddy current data; and
    determining locations of defects in each of the pipes based on the spatial frequency content, wherein the locations of defects are determined based on comparing the eddy current data with spectrograms stored in a memory and associated with defects of a known size and radial distance.

10. The method according to claim 9, further comprising:
    publishing a time-frequency spectrogram derived from the eddy current data in a human-readable format, using shading or color to indicate relative signal strength.

11. The method according to claim 9, further comprising:
    retrieving information from the memory to form a comparison between the information and a time-frequency spectrogram derived from the eddy current data; and determining at least one of a radial distance or a size associated with one or more of the defects, based on the comparison.

12. The method according to claim 9, wherein the concentric pipes comprise at least one production pipe, at least one completion pipe, and a casing.

13. The method according to claim 9, further comprising:

establishing a baseline signal response for the eddy current data by at least one of scanning of a section of pipe without defects or accessing a database that includes baseline data for the concentric pipes; and subtracting the baseline signal response from the eddy current data to pre-process the eddy current data.

14. The method of claim 9, wherein determining the locations of the defects further comprises:

determining a radial distance and azimuthal location of the defects.

15. The method of claim 14, further comprising:

determining the radial distance based on relative permeability of at least one of the concentric pipes.

16. The method according to claim 9, further comprising:

estimating a size of at least one of the defects based on a travel distance of a transmitter and a receiver.

17. The method according to claim 9, further comprising:

estimating a size of at least one of the defects based on a region of impact for the transmitter-receiver pair that is used to acquire the eddy current data.

18. A method, comprising:

moving a transmitter-receiver pair within a first group of concentric pipes to acquire known defect eddy current data;

determining a frequency spread bandwidth associated with the known defect eddy current data and known defects in the first group of concentric pipes; and storing sizes of the known defects and associated values of the frequency spread bandwidth, or values derived from the frequency spread bandwidth, as known defect information in a memory, to enable determination of unknown defect size in a second group of concentric pipes disposed in a geological formation upon access to and comparison with signals received by an inspection transmitter-receiver pair disposed in the second group.

19. The method of claim 18, further comprising:

determining a radial distance of at least one unknown defect associated with the unknown defect size based on the known defect information.

20. The method of claim 19, wherein determining the radial distance comprises comparing spectrograms to minimize a cost function.

* * * * *